US012678123B2

(12) United States Patent
Chou et al.

(10) Patent No.: US 12,678,123 B2
(45) Date of Patent: Jul. 14, 2026

(54) MULTI-DIMENSIONAL ARTIFICIAL INTELLIGENCE AUSCULTATION DEVICE

(71) Applicant: Decentralized Biotechnology Intelligence Co., Ltd., Taipei (TW)

(72) Inventors: Yao-Sheng Chou, Taipei (TW); Wei-Sheng Su, Taipei (TW); Hsiao-Yi Lin, Taipei (TW)

(73) Assignee: Decentralized Biotechnology Intelligence Co., Ltd., Taipei City (TW)

( * ) Notice: Subject to any disclaimer, the term of this patent is extended or adjusted under 35 U.S.C. 154(b) by 299 days.

(21) Appl. No.: 18/485,725

(22) Filed: Oct. 12, 2023

(65) Prior Publication Data

US 2024/0188922 A1 Jun. 13, 2024

(30) Foreign Application Priority Data

Dec. 8, 2022 (TW) .................................. 111147275

(51) Int. Cl.
*A61B 7/02* (2006.01)
*A61B 5/00* (2006.01)
*A61B 5/27* (2021.01)

(52) U.S. Cl.
CPC ................ *A61B 7/026* (2013.01); *A61B 5/27* (2021.01); *A61B 5/6804* (2013.01)

(58) Field of Classification Search
CPC ......... A61B 7/026; A61B 5/27; A61B 5/6804; A61B 5/7264; A61B 7/04
See application file for complete search history.

(56) References Cited

U.S. PATENT DOCUMENTS

2004/0236239 A1* 11/2004 Murray .................. A61B 7/003
600/528
2018/0116626 A1* 5/2018 Darbari .............. A61B 5/02055
2022/0360876 A1* 11/2022 Lin ......................... H04R 1/083

\* cited by examiner

*Primary Examiner* — Eugene T Wu
(74) *Attorney, Agent, or Firm* — WPAT, P.C.; Anthony King

(57) ABSTRACT

A multi-dimensional artificial intelligence auscultation device includes multiple heart sound sensors configured to place on different heart sound auscultation positions of the body to be monitored for simultaneously capturing heart sound signals corresponding to the different heart sound auscultation positions, and a processing unit is electrically coupled to the heart sound sensors to perform pre-processing such as filtering, signal amplification and digitization on the collected heart sound signals. The pre-processed heart sound signals are analyzed and cross-compared by an external computing device to obtain the correlations between individual heart sound signals of the multiple heart sound signals.

15 Claims, 9 Drawing Sheets

500

500

500

MULTI-DIMENSIONAL ARTIFICIAL INTELLIGENCE AUSCULTATION DEVICE

TECHNICAL FIELD

The present invention relates to an auscultation device, more specifically, a multi-dimensional artificial intelligence auscultation device.

BACKGROUND

Heart sound detection device, for example, a stethoscope or auscultation device, is an instrument for diagnosing organ activities by sound detection. The stethoscope or auscultation device is employed to collect the sounds of organ activities, such as the heart/lung, by placing the earpiece on the corresponding inspection positions, and the detected sounds are converted and amplified, followed by transmitting directly to the speakers to allow doctors or medical staffs to determine the disease cause and make precise diagnosis by the sound signal.

Cardiac auscultation is a method of assessing cardiac function and activity in traditional physical inspection. Audible heart sounds are produced by sudden closing of heart valves. In healthy adults, two normal heart sounds occur sequentially during a cycle. The pitch and rate of the heart sounds follow certain regulations.

The first heart sound (S1) occurs at the beginning of ventricular systole due to the closure of the mitral and tricuspid valves (collectively known as the atrioventricular valves). The second heart sound (S2) occurs at the onset of ventricular diastole due to closure of the aortic and pulmonary valves. S1 is base with longer duration, while S2 is shorter duration treble. Under normal conditions, the S1-S2 interval (systole) is shorter than the S2-S1 interval (diastole).

A variety of heart diseases can be effectively diagnosed by auscultation. In some fatal heart diseases, such as acute valvular dysfunction, cardiac auscultation has been proved to be a successful, reliable and low-cost early diagnosis method.

Phonocardiography (PCG) is a method of recording heart sounds for collecting mechanical vibrations generated by heartbeat at various positions on the chest wall by the stethoscope. The recorded heart sounds are presented graphically during this process. PCG provides quantitative and qualitative information on heart sounds and murmurs.

The commonly used auscultation is to inspect different parts of the body one by one by the stethoscope. However, the conventional method cannot simultaneously compare the signal collected from different positions of the identical organ, such as the heart. This amount of information is obviously insufficient for early detection and warning for lesions, especially, heart failure, myocardial infarction and other psychogenic diseases.

Therefore, what is required is a multiple-dimensional detecting device and an analysis method capable of simultaneously measuring sound at multiple positions to obtain the correlation of sounds at different positions.

SUMMARY OF THE INVENTION

Based on above, the purpose of the present invention is to provide multi-dimensional artificial intelligence ausculta- tion device to achieve multiple sensing data from different detecting positions, simultaneously.

In one aspect, the present invention provides a multi-dimensional artificial intelligence auscultation device including multiple heart sound sensors configured at multiple sensing positions to simultaneously capture multiple heart sound signals multiple different positions; a processing device is electrically coupled to the multiple heart sound sensors for processing the multiple heart sound signals; and the multiple heart sound sensors forms a sensing array on a patch. The processing device collects signals of the multiple heart sound sensors that are nearby a user heart. The signal strength of the collected signals is higher than a threshold. The processing device ignores signals under the threshold.

The multiple heart sound sensors include piezoelectric material formed on at least one flexible substrate to sense signals generated by vibration. Conductive electrodes are formed on an upper surface and a lower surface of the piezoelectric material. The piezoelectric material is polyvi- nylidene fluoride (PVDF) polymer piezoelectric or lead zirconate titanate (PZT). The processing device includes a filter electrically connected to the multiple heart sound sensors for receiving and filtering sound signals from the multiple heart sound sensors. A signal amplifier is electri- cally connected to the filter for amplifying the filtered sound signals. The processing device also includes an analog-to-digital converter electrically connected to the signal ampli- fier for digitizing the amplified sound signals.

In another one aspect, a multi-dimensional artificial intel- ligence auscultation device includes: multiple heart sound sensors configured at multiple sensing positions to simulta- neously capture multiple heart sound signals multiple dif- ferent positions, wherein the multiple heart sound sensors forms a sensing array on a patch; a control panel separated from the patch, and the control panel having a processing device electrically coupled to the multiple heart sound sensors for processing signals of the multiple heart sound sensors located nearby a user heart; the signal strength of the collected signals is higher than a threshold. The processing device ignores signals under the threshold.

In one embodiment, the multiple heart sound sensors include piezoelectric material formed on at least one flexible substrate to sense signals generated by vibration. Conduc- tive electrodes are formed on an upper surface and a lower surface of the piezoelectric material. The piezoelectric mate- rial is polyvinylidene fluoride (PVDF) polymer piezoelectric or lead zirconate titanate (PZT). The patch includes a flexible substrate.

DETAILED DESCRIPTION

Some preferred embodiments of the present invention will now be described in greater detail. However, it should be recognized that the preferred embodiments of the present invention are provided for illustration rather than limiting the present invention. In addition, the present invention can be practiced in a wide range of other embodiments besides those explicitly described, and the scope of the present invention is not expressly limited except as specified in the accompanying claims.

The main purpose of the present invention is to provide a multi-dimensional artificial intelligence auscultation device, which is used to simultaneously measure the conditions of different positions, and cross-compare the data to obtain more accurate information.

Figures 1A, 1B:
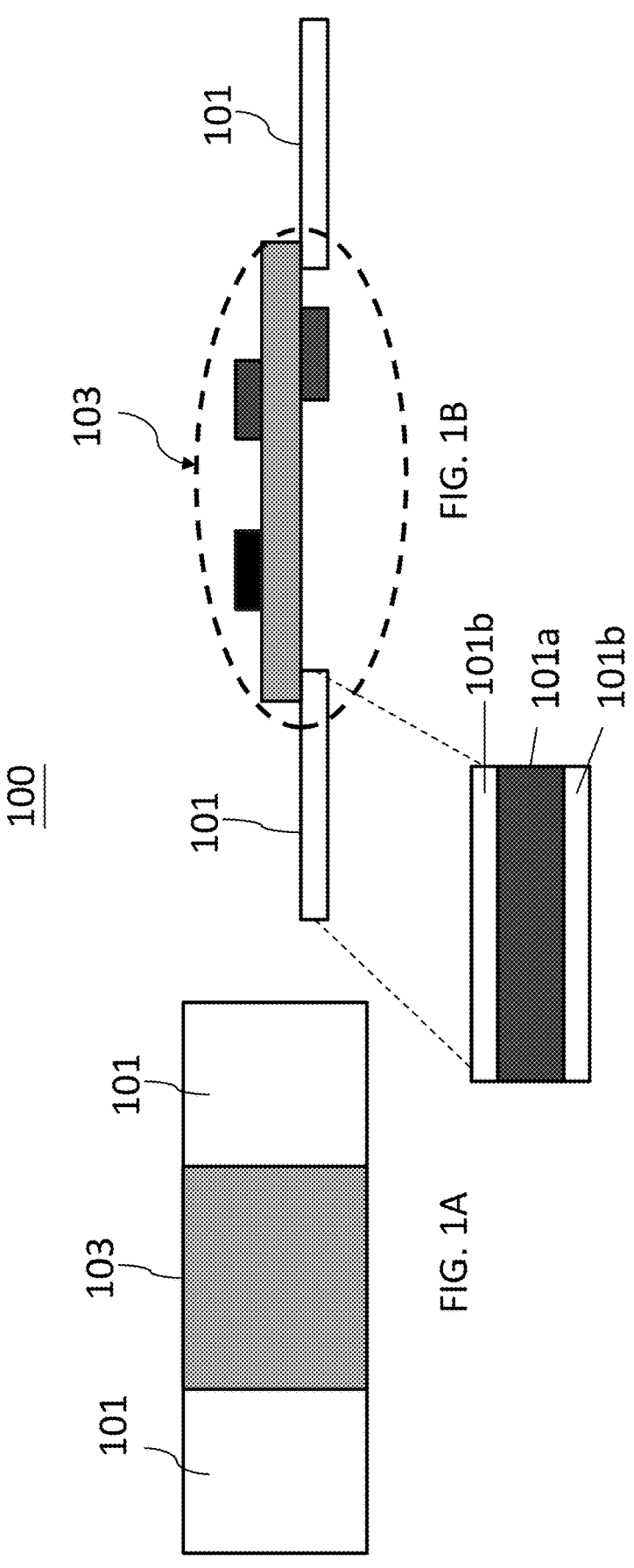
FIG. 1A-FIG. 1B show the multi-dimensional artificial intelligence auscultation device according to an embodiment of the present invention.

FIG. 1A and FIG. 1B show the structure of the multi-dimensional artificial intelligence auscultation device 100 according to one embodiment of the present invention. FIG. 1A shows the top view, the auscultation device includes a heart sound sensor 101 and a driving and detection circuit (hardware module 103) carried by a PCB circuit board. FIG. 1B is the cross-sectional view, the PCB circuit board is provided with a processor, a filter, an A/D converter and other electronic components for collecting sounds, processing the collected sounds and sending the processed sounds to an external computing device for analysis.

In one embodiment, the heart sound sensor 101 is made of a piezoelectric material 101*a*, such as polyvinylidene fluoride (PVDF) polymer piezoelectric, lead zirconate titanate (PZT) and other materials. The conductive metal (for example, aluminum (Al), copper (Cu), etc.) layers 101*b* are formed on the upper and lower surface as electrodes, thereby forming the piezoelectric patch on a flexible substrate to sense the voltage signal generated by vibration.

According to an embodiment of the present invention, the auscultation device includes separated multiple heart sound sensors or these sensors may be formed in an array.

Figure 2A:
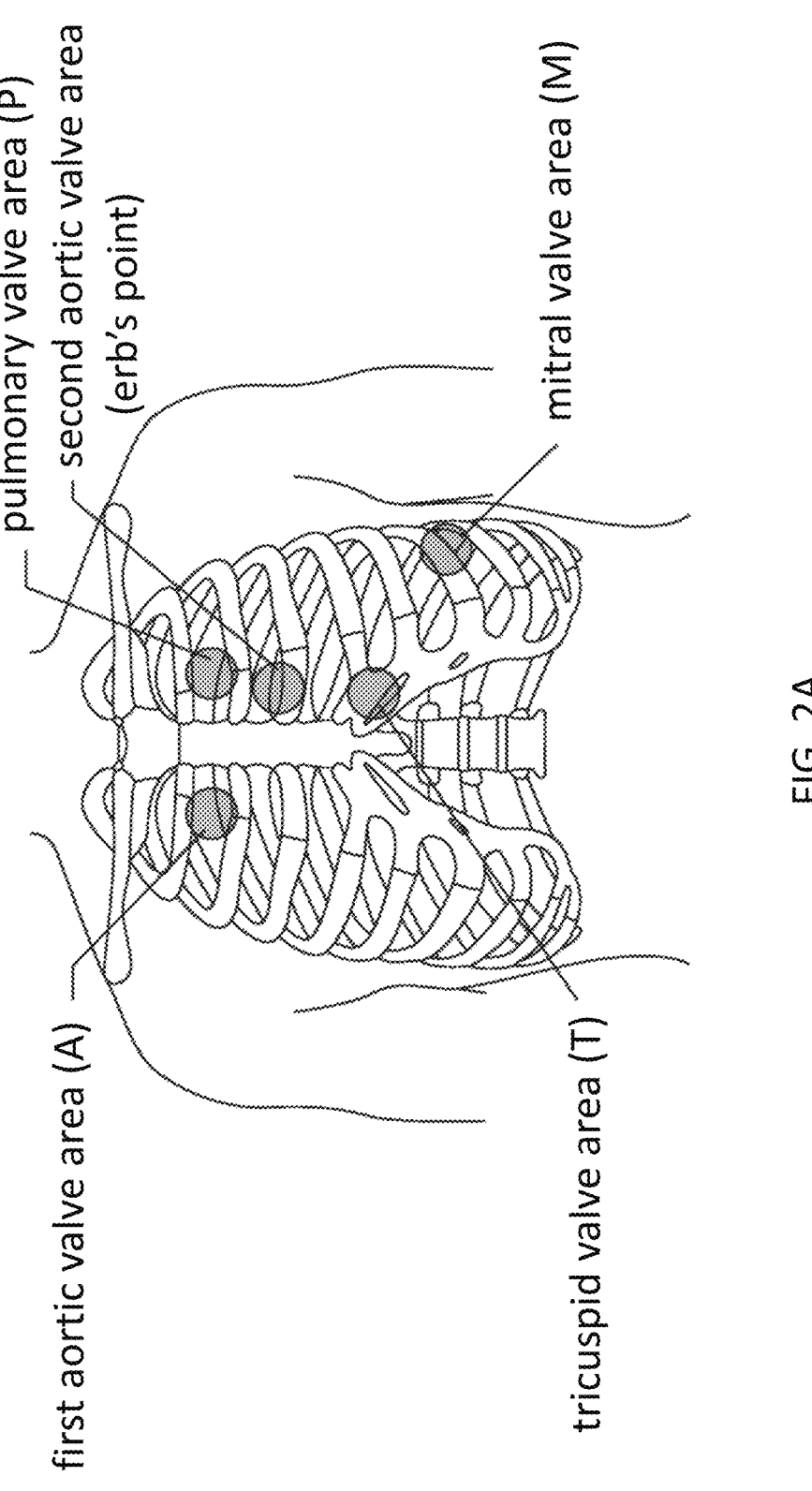
FIG. 2A shows the distribution of the main heart sound inspection areas.
Figure 2B:
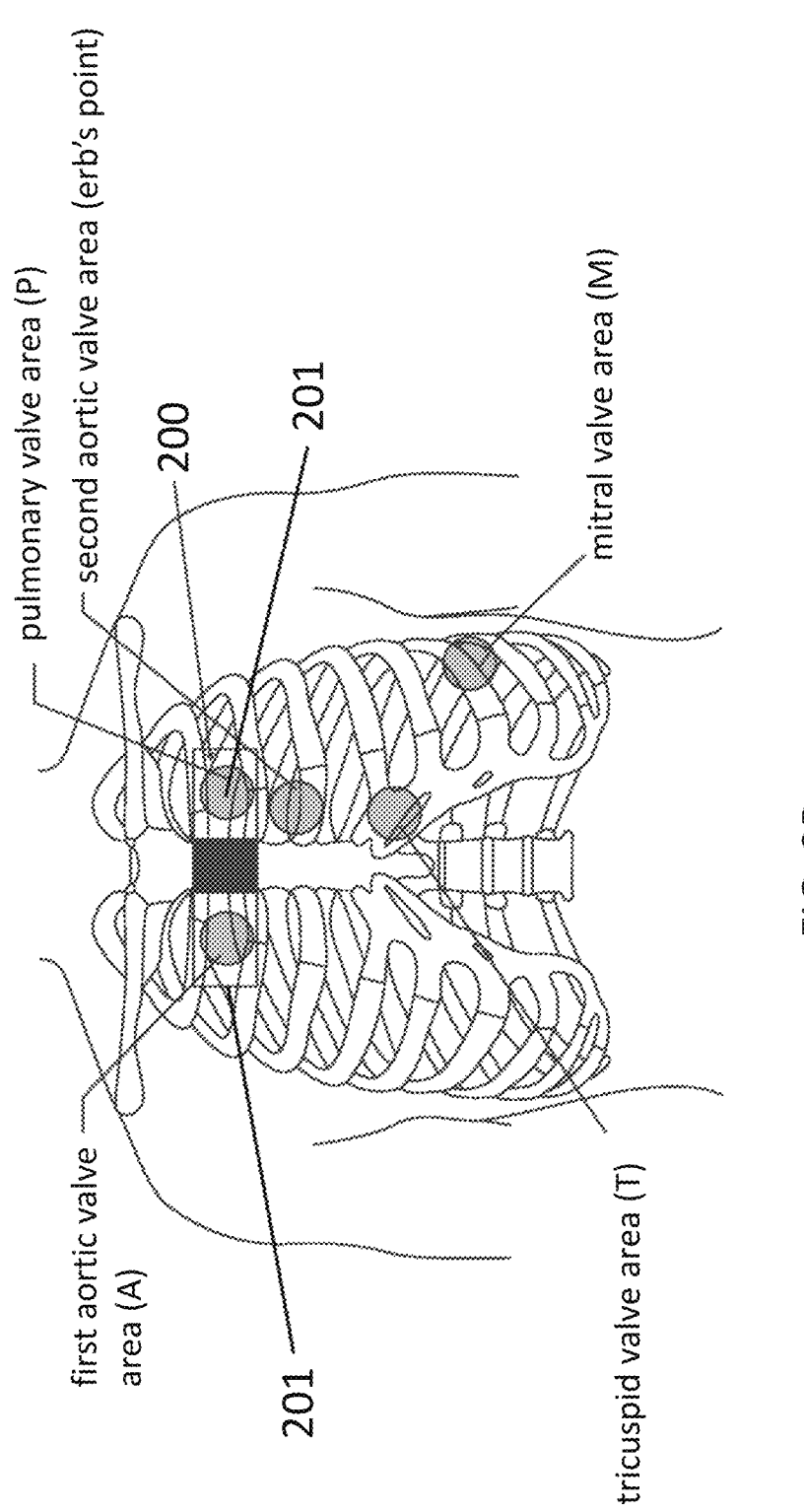
FIG. 2B shows a diagram of the heart sound sensors for the multi-dimensional artificial intelligence auscultation device according to an embodiment of the present invention.
Figure 2C:
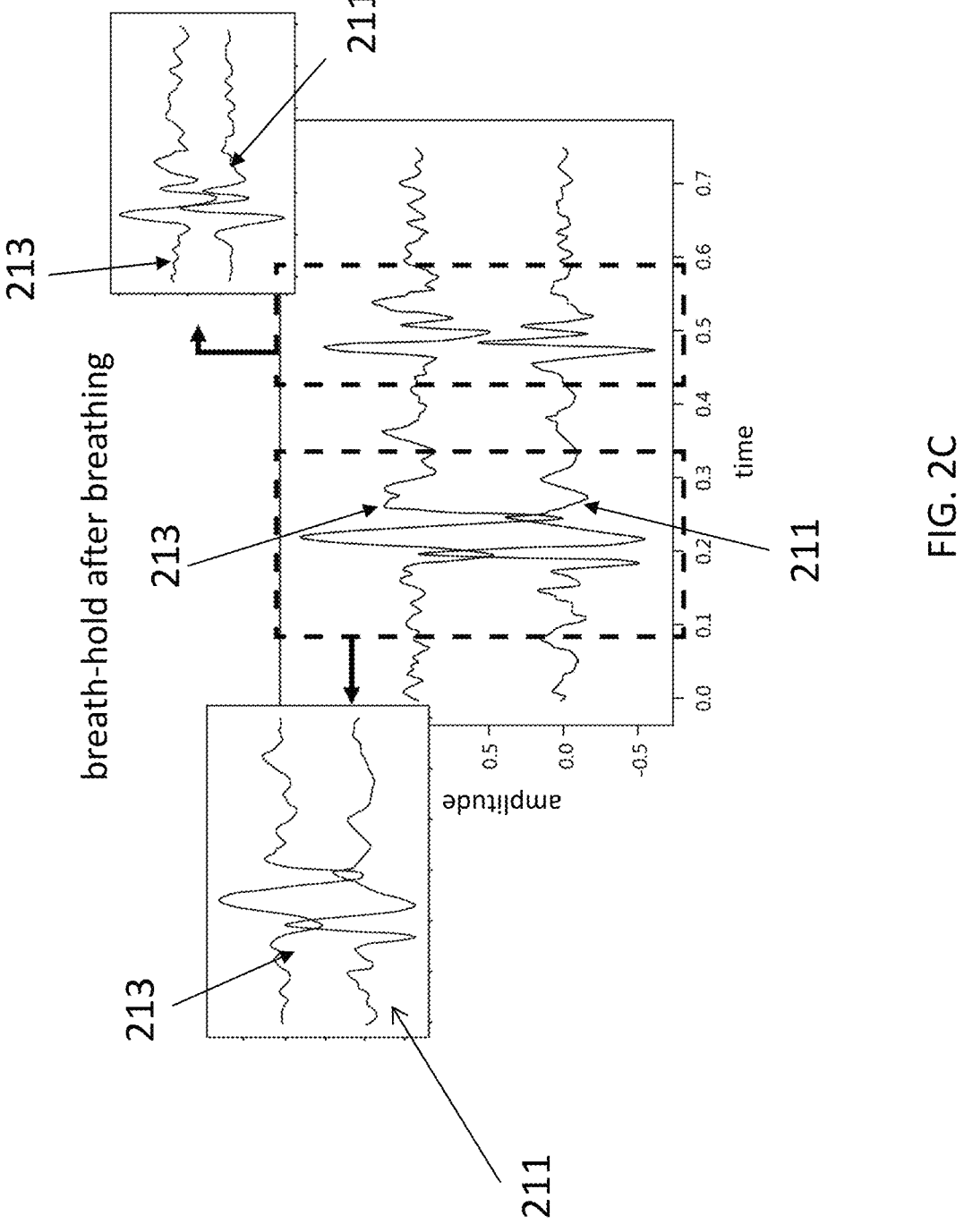
FIG. 2C shows the detected heart sound signals corre- sponding to the aortic valve area (A) and the pulmonary valve area (P) during the breath-hold period after breathing.

FIG. 2A shows the typical main five heart sound detecting areas in clinic, namely, (1) first aortic valve area (A), (2) pulmonary valve area (P), (3) second aortic valve area (Erb), (4) tricuspid valve area (T), and (5) mitral valve area (M). In the embodiment of the present invention, the heart sound sensors simultaneously measure sounds from multiple positions for cross-comparing the sounds correlation among them. FIG. 2B shows a schematic diagram of multiple heart sound sensors 201 for a multi-dimensional artificial intelligence auscultation device 200. In the figure, the multiple heart sound sensors 201 are provided to simultaneously measure the heart sound signals of the first aortic valve area (A) and the pulmonary valve area (P). FIG. 2C shows the detected heart sound signals corresponding to the first aortic valve area (A) and the pulmonary valve area (P) during the breath-hold period after breathing. The signal 211 is the heart sound measured by the multiple heart sound sensors in the first aortic valve area (A), and the signal 213 refers to the heart sound measured by the heart sound sensors in the pulmonary valve area (P). By synchronously measuring the heart sound signal at the two positions, the time difference between the valve opening/closing at two measurement positions is achieved, thereby obtaining the reversed splitting time. The paradoxical or reversed splitting is the result of a delay in the aortic closure sound. Therefore, the present invention can monitor specific symptoms signals at any time to avoid acute situation, for example, acute myocardial infarction.

Figure 3:
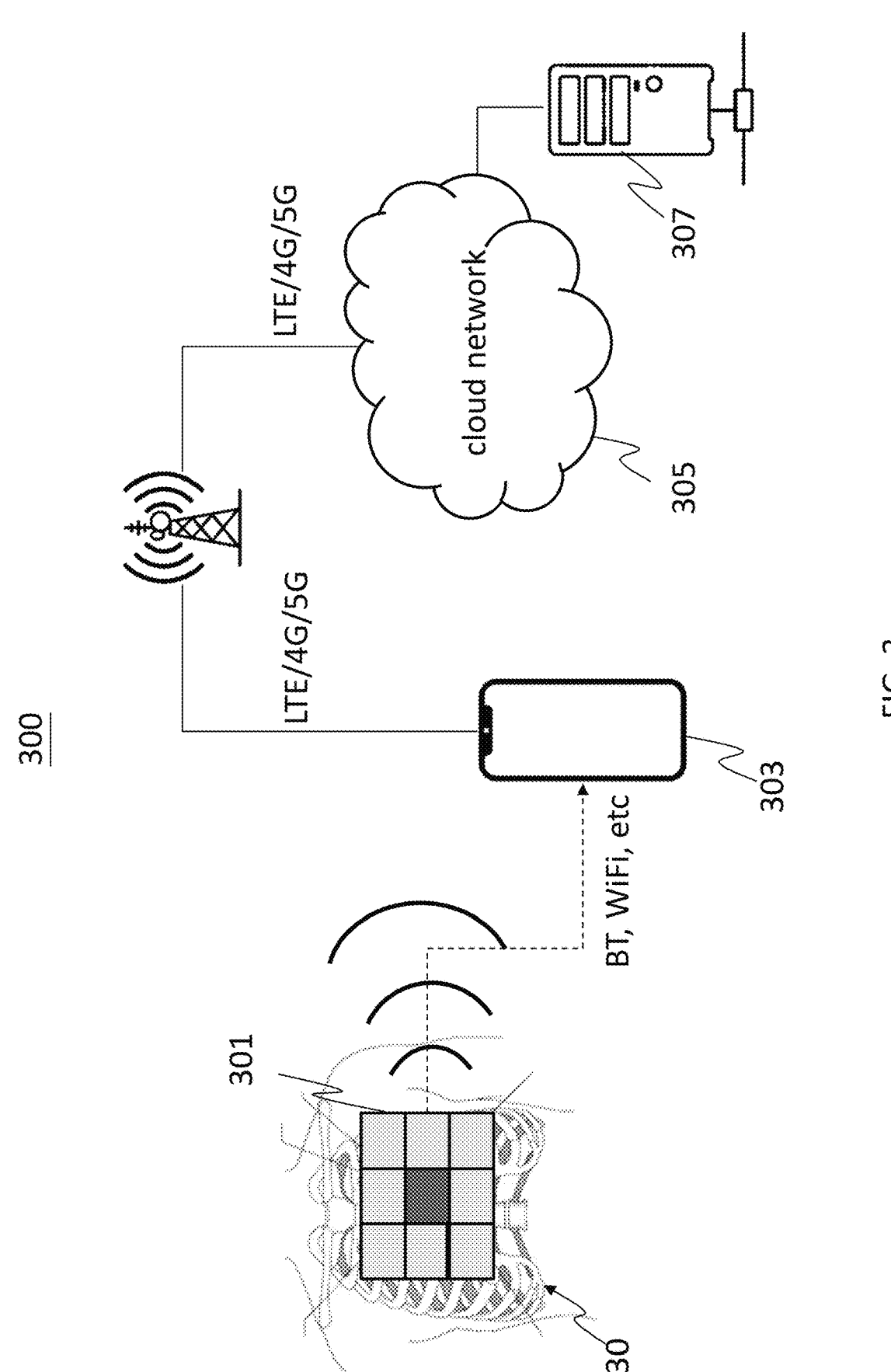
FIG. 3 shows a system diagram according to one embodi- ment of the present invention.

As shown in FIG. 3, the multi-dimensional artificial intelligence auscultation device 300 includes a plurality of heart sound sensors 301 pasted on the user 30 with the form of monitoring patches. The multi-dimensional artificial intelligence auscultation device 300 is coupled with a mobile device (the external computing device) 303, for example, a smart phone, a tablet computer. The heart sound collected by the multi-dimensional artificial intelligence auscultation device 300 is uploaded to the cloud server 307 from the mobile device 303 via the cloud network 305 through wireless transmission (for example, Bluetooth and WiFi). In the cloud server, the data is stored in the cloud data database. The above system also includes an application program installed in the mobile device, the application program includes instructions for receiving and sending data among the multi-dimensional AI auscultation device 300, the mobile device 303 and the cloud server 307. The application program is operated based on the Android, Windows 10 or iOS operating system platform, and application program is provided to upload the collected data/signals, such as heart sound signals and their waveforms, to the cloud server 307 for storage, followed by analyzing the data through feature extraction and algorithm to generate an evaluation report for medical advice.

Figure 4:
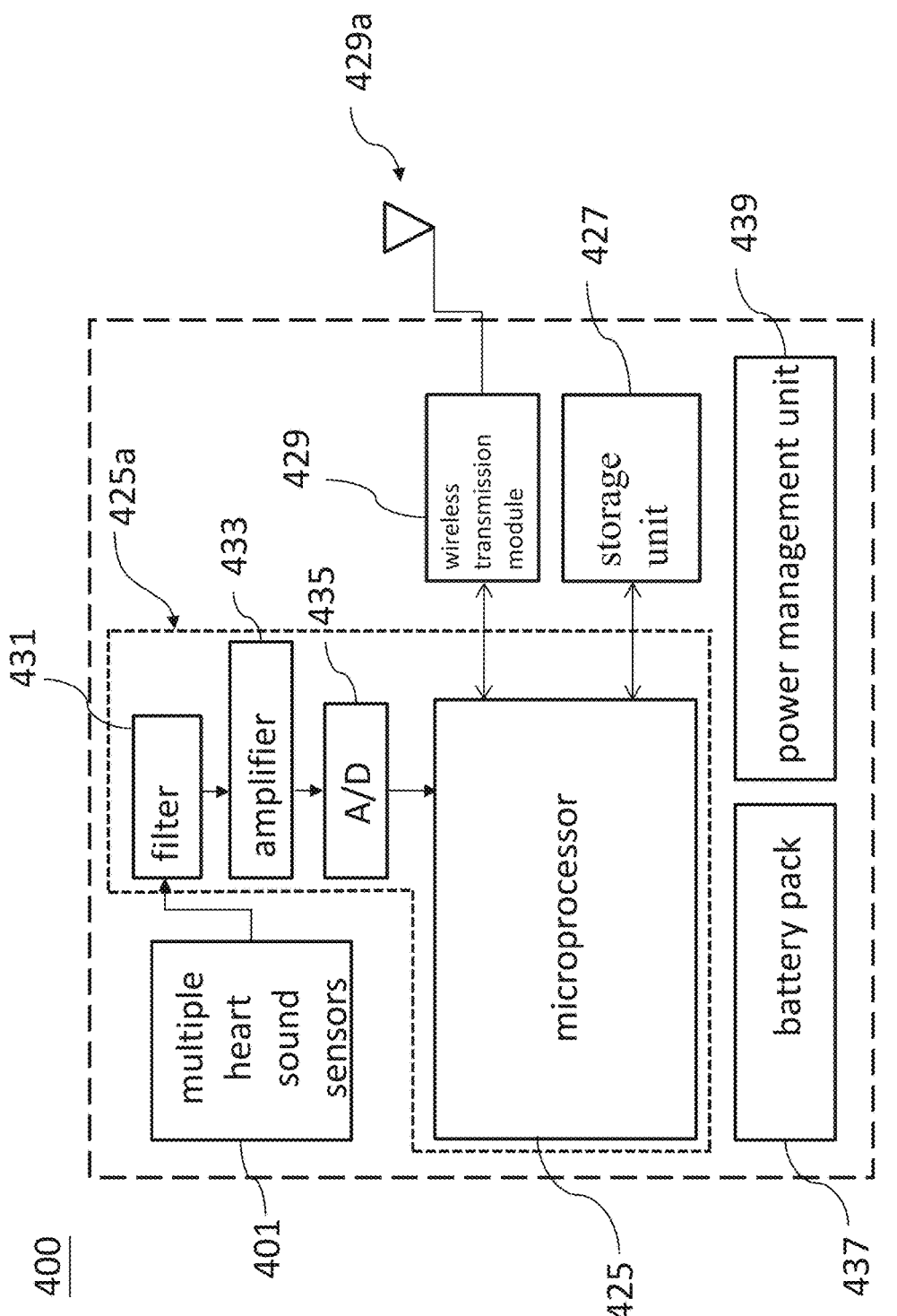
FIG. 4 shows the functional diagram of the multi-dimen- sional artificial intelligence auscultation device according to one embodiment of the present invention.

The multi-dimensional AI auscultation device 400 includes multiple heart sound sensors 401. FIG. 4 shows the functional block diagram of the present invention. The multi-dimensional AI auscultation device 400 fetches the sounds by the heart sound sensors 401 for physiological monitoring and remote diagnosis. The multi-dimensional AI auscultation device 400 can receive and transmit data, and execute software applications, which includes a microprocessor, a storage unit, and a wireless transmission module.

The microprocessor 425 may be a microcontroller, a digital signal processor (DSP), an application-specific integrated circuit (ASIC), a programmable logic circuit, or other digital data processing devices that execute instructions to perform processing operations according to the present invention. The microprocessor 425 can execute various application programs stored in the storage unit.

The storage unit 427 may include read only memory (ROM), random access memory (RAM), electrically erasable programmable ROM (EEPROM), flash memory, or any memory commonly used in computers.

The wireless transmission module 429 is connected to the antenna 429*a* which is configured to transmit and receive data through a wireless communication channel. The wireless communication channel can be any type of wireless communication protocol, such as WiFi, Bluetooth, RFID, NFC, 3G/4G/5G or any other wireless communication interface.

The sound signal is obtained from the human body through the multiple sound sensors 401, the noise is filtered out by a filter 431 and is amplified by a signal amplifier 433. The filtered/amplified signal is converted by an analog to digital converter (ADC) 435 from analog signals into digital signals, followed by processing by the microprocessor 425 to obtain de-noising and stable ECG and heart sound signals. The microprocessor 425 stores the de-noising and stable sound signals in the storage unit through instructions or programs. The signals may be sent to the mobile devices (such as smartphone) by the wireless transmission module 429 for further analysis.

The battery pack 437 provides power for the multi-dimensional artificial intelligence auscultation device 400, and is cooperate with the power management unit 439 to optimize the power utilization.

The aforementioned signal amplifier 433, the filter 431, the analog-to-digital converter 435 and the microprocessor 425 can be integrated into an integrated circuit (IC) as the control device 425a of the multi-dimensional AI auscultation device 400.

The heart sound signals include several different section types, such as S1 section, S2 section, S3 section, S4 section, murmur section, wherein S1 (first sound) is generated by vibrations created by the closing of these two valves, mitral and tricuspid valve. The aortic and pulmonic valves close and cause vibrations, giving rise to the second heart sound, the third heart sound S3 is a low-pitched sound audible with the rapid rush of blood from the atrium into the ventricle as it starts relaxing. The fourth S4 is a low-intensity sound heard just before S1 in the cardiac cycle. The sudden slowing of blood flow by the ventricle as the atrium contracts causes this sound, which may be a sign of heart disease. The murmur is most likely caused by blood turbulence. S1 may further include M1 caused by the mitral valve, and T1 caused by the tricuspid valve. The S2 may further include A2 caused by the aortic valve and P2 caused by the pulmonary valve. For healthy individuals, S3, S4 and murmurs are usually inaudible.

Because the body sounds, such as heart sounds, effectively reflects the heart conditions, especially, the valve activity and blood flow status. For example, the closing of the atrioventricular valve is the main factor to generate the first heart sound, and the second heart sound is generated when the semilunar valve is closed. For many cardiovascular diseases, especially valvular diseases, the heart sounds are important information for diagnosis, therefore, the heart sounds are widely used for clinic.

According to one embodiment, the output terminals of the plurality of sound sensors 401 are processed by signal amplifiers, the filters and the analog-to-digital converters, and the noise-free and digitized signal is stored in the storage unit of multi-dimensional AI auscultation device.

In one embodiment, the digitized ECG and sound signal in the storage unit of the multi-dimensional AI auscultation device 400 is sent to the processing system of the mobile device 303 via wireless transmission. Alternatively, these signals may be processed by the computing system in the cloud server 307 for further processing, analysis and saving.

Figures 5, 6:
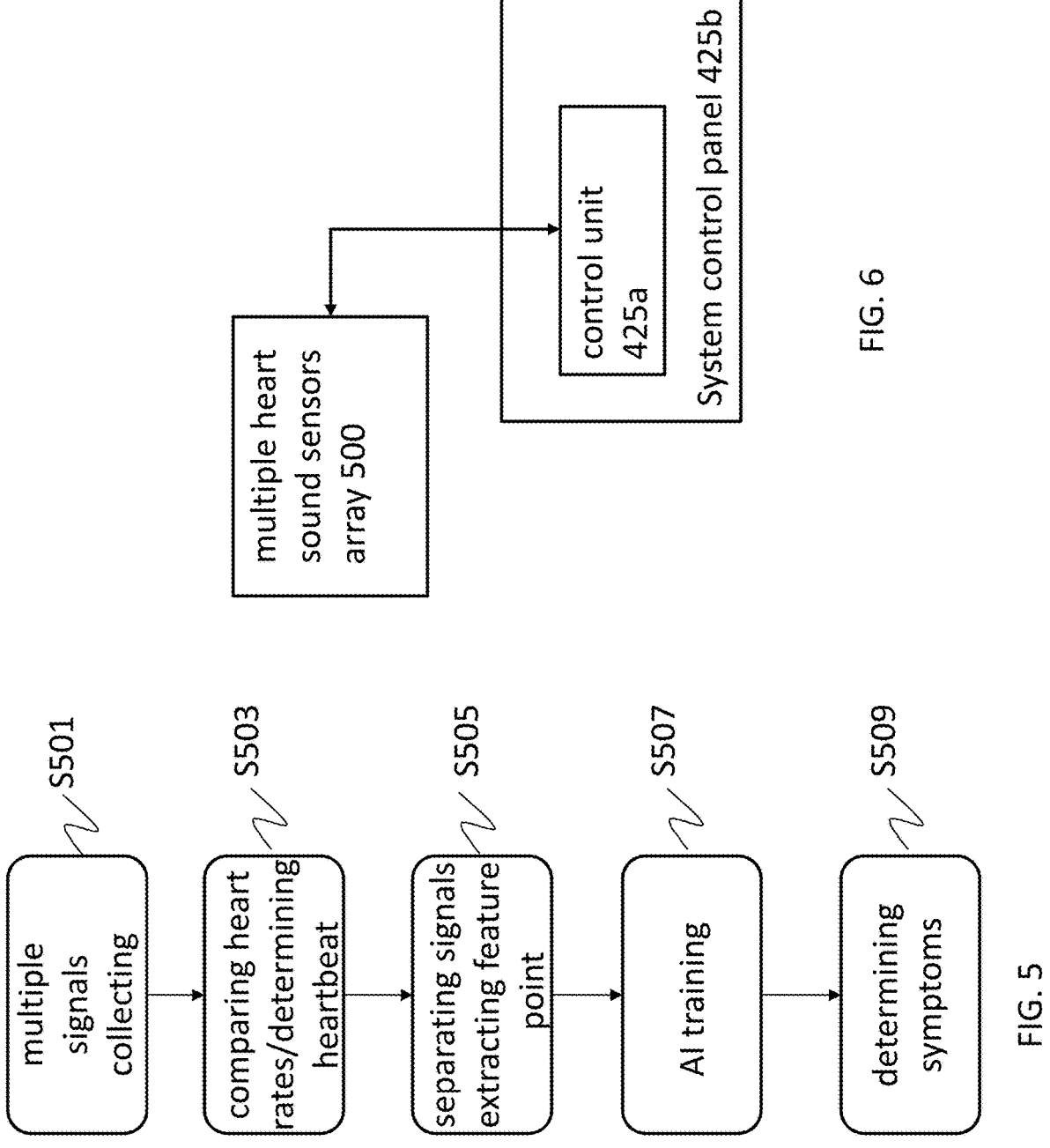
FIG. 5 shows the heart sound data analysis process according to the present invention.
FIG. 6 shows the control panel and the sensor patch according to the present invention.

In one embodiment, the analysis flow of the heart sound data is shown in FIG. 5. In step S501, multiple heart sound signals are simultaneously collected by the multiple sound sensors 401 of the auscultation device 400 at different positions, followed by performing heart sound signal analyses, pre-processing (such as filtering and amplification) and digitalization. In step S503, the pre-processed/digitized heart sound signals are sent to the external computing device, and the processor analyzes and compares the heart rates to determine the correct heartbeat. In step S505, the processor separates the sound signals of the correct heartbeat, and extracts the feature point of the sound signal. Subsequently, in step S507, the processor compares, classifies, analyzes, and trains the extracted feature points with the data pre-stored in database by AI algorithms or machine learning. Later, in step S509, the processor determines the symptoms based on the results of the classification, the comparison, the analysis and the training.

In one embodiment, the AI or machine learning algorithms may be executable computing programs or application programs of the external computing device.

In one embodiment, the external computing device may be a mobile device (for example, a smart phone) or a cloud server.

In one embodiment, the above AI or machine learning algorithms may include the following steps: prefiltering and normalizing the input heart sound signal by the processor; extracting the time domain and frequency domain features by the processor; outputting the classification results by convolutional neural network (CNN) model or other types of neural network models (such as RNN/LSTN, etc.). The RNN is a recurrent neural network model and LSTM refers to a long-term short-term memory model.

The advantages of the present invention: the heart sound signals are simultaneously collected at different positions; the correct heartbeat is determined by comparing the heart rate at each position; the preliminary diagnosis of the heart condition is realized by the relationship of heart sounds, thereby reducing the dependence on professionals; and the cardiac abnormalities are automatic identified for home monitoring.

The sensor signal is poured out through the signal transmission line and wirelessly transmitted to the control panel for analysis.

Signal transmission lines can be flexible circuit boards, coaxial cables, etc.

Figure 8:
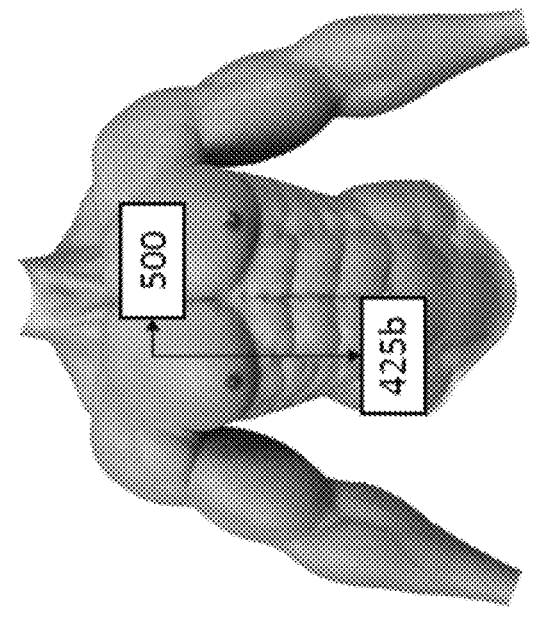
FIG. 8 shows the control panel and the sensor array patch attached on the user according to the present invention.
Figure 7:
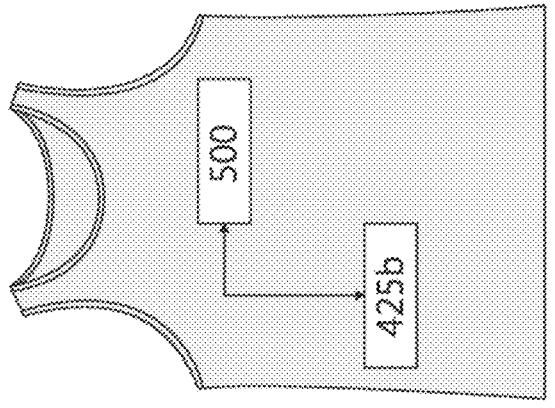
FIG. 7 shows the control panel and the sensor array patch formed on the clothing according to the present invention.

In one example, the multiple sensors are formed with an array form on the patch. The multiple heart sound sensor array 500 is separated from the system control panel 425b including the control device 425a as shown in FIG. 6. In one embodiment, both the sensor array 500 and the system control panel 425b are made of flexible material, they are likely to be integrated into clothing, as shown in FIG. 7. Due to the small size of the control panel 425b, it will not cause uncomfortable to the user. During operation, the control panel 425b can be attached anywhere on the user body, such as the waist and armpit. The control panel 425b can be a hard board or a flexible circuit board, as shown in FIG. 8.

Figure 10:
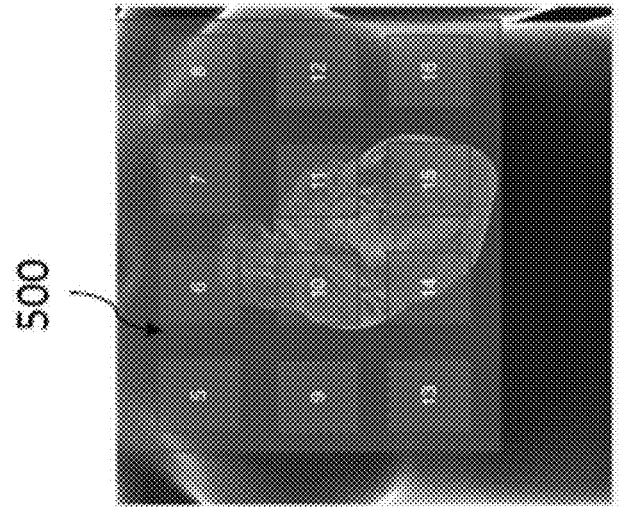
FIG. 10 shows the sensor array patch attached on the user according to the present invention.
Figure 10:
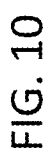
Figure 9:
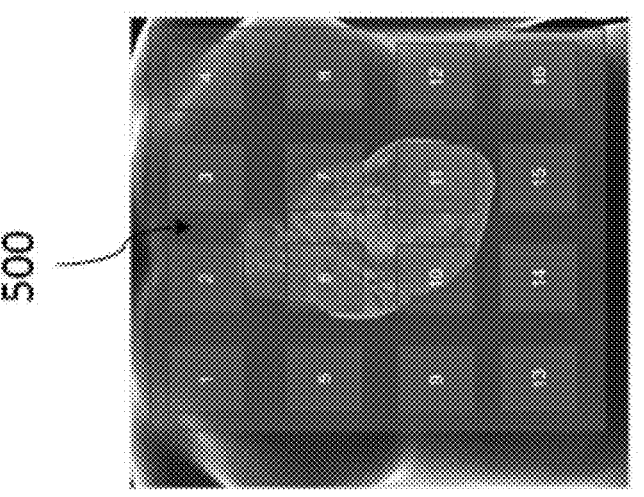
FIG. 9 shows the sensor array patch attached on the user according to the present invention.

Preferably, please refer to FIG. 9, each one sensor of the multiple sensor array 500 on the patch has a code or index to allow the control device 425a to distinguish each individual sensor with one another. A signal strength threshold is predetermined set in the control device 425a. Only the signal that is beyond the signal threshold will be collected, otherwise, the signal will be ignored. For example, when the patch is worn on the user for detecting the heart sound signal, the sensors 6, 7, 10, 11 are located nearby the heart, the signal of these sensors 6, 7, 10, 11 will be collected due to their signal strength is above the threshold. Other signals of the sensors 1, 2, 3, 4, 5, 8, 9, 12, 13, 14, 15, 16 that far away from the heart will be filtered out or be ignored. The design will fetch the best signals for the heart sound collecting, thereby improving the accuracy and efficiency. Referring to FIG. 10, if the patch is at the improper positions, the control device 425a will receive the signal of the sensors 10, 11, 14, 15 to replace the original sensors due to the signal strengths of these sensors 10, 11, 14, 15 are better than others. Consequently, the control device 425a will receive the best signal at all time even the patch is not at the proper position. Alternatively, the control device 425*a* is preset to collect the signals of the sensors nearby the user heart.

As will be understood by persons skilled in the art, the foregoing preferred embodiment of the present invention illustrates the present invention rather than limiting the present invention. Having described the invention in connection with a preferred embodiment, modifications will be suggested to those skilled in the art. Thus, the invention is not to be limited to this embodiment, but rather the invention is intended to cover various modifications and similar arrangements included within the spirit and scope of the appended claims, the scope of which should be accorded the broadest interpretation, thereby encompassing all such modifications and similar structures. While the preferred embodiment of the invention has been illustrated and described, it will be appreciated that various changes can be made without departing from the spirit and scope of the invention.

What is claimed is:

1. A multi-dimensional artificial intelligence auscultation device includes:

multiple heart sound sensors configured at multiple sensing positions to simultaneously capture multiple heart sound signals at multiple different positions; and a processing device electrically coupled to said multiple heart sound sensors for processing said multiple heart sound signals, wherein said multiple heart sound sensors forms a sensing array on a patch, wherein said processing device collects signals of said multiple heart sound sensors nearby a user heart, and said patch is configured to cover an area near said user heart with a first portion of said heart sound sensors adjacent to said user heart and a second portion of said heart sound sensors distanced from said user heart, and wherein a signal strength of said signals collected from said first portion of said heart sound sensors is higher than a threshold and a signal strength of said signals collected from said second portion of said heart sound sensors is under said threshold, and said processing device is configured to ignore said signals having said signal strength under said threshold.

2. The device of claim 1, wherein said multiple heart sound sensors includes piezoelectric material formed on at least one flexible substrate to sense signals generated by vibration.

3. The device of claim 2, wherein conductive electrodes are formed on an upper surface and a lower surface of said piezoelectric material.

4. The device of claim 2, wherein said piezoelectric material is polyvinylidene fluoride (PVDF) polymer piezoelectric.

5. The device of claim 2, wherein said piezoelectric material is lead zirconate titanate (PZT).

6. The device of claim 1, wherein said processing device includes a filter electrically connected to said multiple heart sound sensors for receiving and filtering sound signals from said multiple heart sound sensors.

7. The device of claim 6, wherein said processing device includes a signal amplifier electrically connected to said filter for amplifying said filtered sound signals.

8. The device of claim 7, wherein said processing device includes an analog-to-digital converter electrically connected to said signal amplifier for digitizing said amplified sound signals.

9. The device of claim 8 wherein said processing device includes a microprocessor electrically connected to said analog-to-digital converter to obtain noise free signals.

10. A multi-dimensional artificial intelligence auscultation device includes:

multiple heart sound sensors configured at multiple sensing positions to simultaneously capture multiple heart sound signals at different positions, wherein said multiple heart sound sensors forms a sensing array on a patch; and a control panel separated from said patch, and said control panel having a processing device electrically coupled to said multiple heart sound sensors for processing signals of said multiple heart sound sensors located nearby a user heart, wherein said patch is configured to cover an area near said user heart with a first portion of said multiple heart sound sensors adjacent to said user heart and a second portion of said multiple heart sound sensors distanced from said user heart, and wherein a signal strength of said signals collected from said first portion of said multiple heart sound sensors is higher than a threshold and a signal strength of said signals collected from said second portion of said multiple heart sound sensors is under said threshold, and said processing device is configured to ignore said signals having said signal strength under said threshold.

11. The device of claim 10, wherein said multiple heart sound sensors includes piezoelectric material formed on at least one flexible substrate to sense signals generated by vibration.

12. The device of claim 11, wherein conductive electrodes are formed on an upper surface and a lower surface of said piezoelectric material.

13. The device of claim 11, wherein said piezoelectric material is polyvinylidene fluoride (PVDF) polymer piezoelectric film.

14. The device of claim 11, wherein said piezoelectric material is lead zirconate titanate (PZT).

15. The device of claim 10, wherein said patch includes a flexible substrate.

* * * * *